United States Patent [19]
de Jager et al.

[11] 3,966,787
[45] June 29, 1976

[54] PROCESS FOR THE PREPARATION OF GRANULAR OR PULVERULENT ORGANIC PEROXIDES

[75] Inventors: Johannes de Jager, Diepenveen; Hendrik Hansma, Schalkhaar, both of Netherlands

[73] Assignee: Akzo N.V., Arnhem, Netherlands

[22] Filed: June 10, 1974

[21] Appl. No.: 477,849

[30] Foreign Application Priority Data
June 14, 1973 Netherlands............... 7308250

[52] U.S. Cl............................. 260/463; 260/610 D
[51] Int. Cl.$^2$.................. C07C 68/00; C07C 179/14
[58] Field of Search........................ 260/463, 610 D

[56] References Cited
UNITED STATES PATENTS 2,491,397  12/1949  Stevens............................ 260/463
3,367,951  2/1968  Nielsen et al................... 260/610 D

*Primary Examiner*—Joseph Paul Brust
*Attorney, Agent, or Firm*—Stevens, Davis, Miller & Mosher

[57] ABSTRACT

A process is disclosed for the preparation of granular or pulverulent organic peroxides which are solid at temperatures ranging from −20° to 55°C by solidifying the peroxide in liquid form with a liquid cooling medium which at most hardly dissolves the peroxide, which is liquid at a temperature of −20°C or lower, and which is gaseous at the storage temperature of the peroxide to be solidified. An example of the liquid cooling medium is liquid nitrogen and an example of the organic peroxide is diisopropylperoxydicarbonate. The present process permits the formation of granular or pulverulent solid organic peroxides without traces of liquid peroxide which can cause safety problems.

6 Claims, No Drawings

PROCESS FOR THE PREPARATION OF GRANULAR OR PULVERULENT ORGANIC PEROXIDES

The present invention relates to a process for preparing granular or pulverulent organic peroxides which are solid at temperatures ranging from −20° to 55°C.

It is known that diisopropylperoxydicarbonate can be obtained by reacting the corresponding chloroformate with an aqueous basic solution of hydrogen peroxide at a temperature of 8° to 10°C. Upon termination of the reaction, the liquid peroxide is isolated and dried and, since it is not stable at temperatures about 0°C, solidified by being poured out into cooling reservoirs.

This method of solidification has the drawback that the heat evolved cannot be removed quickly enough and therefore, as a result of insufficient cooling, liquid diisopropylperoxydicarbonate may remain inside the block of peroxide so obtained, which is undesirable from considerations of safety. Moreover, the blocks of cooled diisopropylperoxydicarbonate can only be removed from the cooling reservoirs with difficulty and the lumps of diisopropylperoxydicarbonate obtained are difficult to handle and to measure.

Consequently, there is, in practice, a need for a safe, easy-to-handle and readily-measurable, granular or pulverulent diisopropylperoxydicarbonate and other organic peroxides.

It has now been found that organic peroxides which are solid at temperatures ranging from −20° to 55°C may be obtained in a granular or pulverulent form in a simple way, by solidifying the liquid peroxide with the aid of a liquid cooling medium in which the subject peroxide does not dissolve or hardly dissolves, the cooling medium being liquid at a temperature of −20°C or lower, but gaseous at the storage temperature of the subject peroxide.

By storage temperature is meant the temperature at which the peroxide may be stored safely and without considerable loss of active oxygen for at least 3 months.

The process according to the invention has the advantage that the heat of solidification generated may be removed very quickly by evaporating the cooling medium, the granules obtained are solid into the core and do not cake together so inclusion of the cooling medium in the peroxide is avoided.

Examples of organic peroxides which may be obtained in granular or pulverulent form according to the invention are:

| Peroxide | Melting Point °C | Storage temp.°C |
| --- | --- | --- |
| diisopropylperoxydicarbonate | 6–8 | ≤ −10 |
| di-n-decylperoxydicarbonate | 15–20 | ≤ +10 |
| di-octanoylperoxide | 18–20 | ≤ +10 |
| di-pelargonylperoxide | 10–11 | 0 |
| di-decanoylperoxide | ± 40 | 10 |
| di-lauroylperoxide | 52 | ≤ 35 |

Liquid nitrogen is preferably used as the cooling medium. Immediately after its preparation, when the peroxide is still in the liquid phase, such as for example in the preparation of diisopropylperoxydicarbonate, or otherwise after melting, for example in the preparation of di-lauroyl-peroxide, the peroxide may be brought into contact with the cooling medium in any suitable way, e.g. by simultaneously measuring out the liquid peroxide and the cooling medium. Preferably, the liquid peroxide is sprayed, atomised into or added drop-wise to a reservoir containing the cooling medium at the temperature desired. The solid peroxide may be removed from this reservoir in a simple way, for example by scooping it out, or it may be isolated by the total evaporation of the cooling medium. The quantity of cooling medium to be used and the temperature of this medium depend upon the ambient temperature and the nature of the material of the cooling reservoir.

The following example illustrates the invention.

EXAMPLE

In the manner described in British patent specification No. 596,779 and starting from isopropylchloroformate, hydrogen peroxide and sodium hydroxide, diisopropylperoxydicarbonate was obtained in liquid form. After washing, the liquid peroxide was poured into liquid nitrogen.

A granular, non-caking product was obtained.

In an analogous way, granular non-caking di-lauroyl-peroxide was obtained by melting solid di-lauroyl-peroxide in water, isolating the liquid peroxide and pouring it out into liquid nitrogen.

What is claimed is:

1. A process for preparing a granular or pulverulent diacyl peroxide which is solid at a temperature ranging from −20° to +55°C, which comprises solidifying a liquid diacyl peroxide with the aid of a liquid cooling medium in which the peroxide is substantially insoluble and which is liquid at a temperature of −20°C or lower, but gaseous at the storage temperature of the diacyl peroxide to be solidified.

2. The process of claim 1, in which the peroxide is solidified in liquid nitrogen.

3. The process of claim 1 wherein said organic peroxide is selected from the group consisting of diisopropylperoxydicarbonate, di-n-decylperoxydicarbonate, di-octanoylperoxide, di-pelargonylperoxide, di-decanoylperoxide, and dilauroylperoxide.

4. A process for solidifying a liquid diacyl peroxide which is a solid at from −20°C to +55°C which comprises mixing said diacyl peroxide while a liquid with a liquid cooling medium in which the peroxide is substantially insoluble and which is a liquid at a temperature of −20°C or lower but gaseous at the storage temperature of the diacyl peroxide to be solidified, whereby heat generated by solidication of the peroxide is removed quickly by evaporation of the liquid cooling medium and discrete granules solid to the core are formed.

5. The process of claim 4 wherein the peroxide is added as a spray to the liquid in which it is insoluble.

6. The process of claim 4 wherein the peroxide is added drop-wise to the liquid in which it is substantially insoluble.

* * * * *